(12) United States Patent
Suzuki (10) Patent No.: US 10,173,032 B2
(45) Date of Patent: Jan. 8, 2019

(54) CATHETER

(71) Applicant: Terumo Kabushiki Kaisha, Shibuya-ku, Tokyo (JP)

(72) Inventor: Kenta Suzuki, Shizuoka (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 463 days.

(21) Appl. No.: 15/075,680

(22) Filed: Mar. 21, 2016

(65) Prior Publication Data

US 2016/0271361 A1  Sep. 22, 2016

(30) Foreign Application Priority Data

Mar. 20, 2015 (JP) ................. 2015-058499

(51) Int. Cl.
*A61M 25/00* (2006.01)
*A61M 25/10* (2013.01)

(52) U.S. Cl.
CPC ........ *A61M 25/0045* (2013.01); *A61M 25/10* (2013.01); *A61M 25/104* (2013.01); *A61M 2025/0046* (2013.01); *A61M 2025/0047* (2013.01); *A61M 2025/1043* (2013.01)

(58) Field of Classification Search
CPC ............ A61M 25/0045; A61M 25/104; A61M 25/10; A61M 2025/1043; A61M 2025/0046; A61M 2025/0047
See application file for complete search history.

(56) References Cited

U.S. PATENT DOCUMENTS

| 5,538,510 A | 7/1996 | Fontirroche |
| 5,820,594 A | 10/1998 | Fontirroche et al. |
| 5,843,032 A | 12/1998 | Kastenhofer |
| 8,900,652 B1 | 12/2014 | Caballero et al. |
| 2009/0162531 A1 | 6/2009 | Nesbitt |
| 2010/0087789 A1 | 4/2010 | Leeflang et al. |

FOREIGN PATENT DOCUMENTS

| JP | 8-33705 A | 2/1996 |
| JP | 2002-119599 A | 4/2002 |
| JP | 2002-301160 A | 10/2002 |
| JP | 2007-325639 A | 12/2007 |
| WO | 03/004248 A1 | 1/2003 |
| WO | 2011/070844 A1 | 4/2013 |

OTHER PUBLICATIONS

The extended European Search Report dated Aug. 31, 2016, by the European Patent Office in corresponding European Application No. 16160036.6. (9 pages).
Office Action ("Notification of Reasons for Refusal") dated Aug. 28, 2018 for Japanese Patent Application No. 2015-058499 (English translation only).

*Primary Examiner* — Michael C Miggins (74) *Attorney, Agent, or Firm* — Buchanan Ingersoll & Rooney PC (57) ABSTRACT

A catheter is provided having a catheter tube which has excellent interlayer bonding strength between a polyamide-based resin and a modified polyolefin resin, and which can ensure visibility with a suitable color degree. A catheter is provided having a catheter tube. The catheter tube includes a first polyamide layer, a modified polyolefin layer arranged on an inner surface of the first polyamide layer, and a second polyamide layer arranged on an outer surface of the first polyamide layer. Among the first polyamide layer, the second polyamide layer, and the modified polyolefin layer, only the second polyamide layer includes a coloring agent.

21 Claims, 2 Drawing Sheets

CATHETER

CROSS-REFERENCES TO RELATED APPLICATION

This application claims the benefit of priority of Japanese Application No. 2015-058499 filed on Mar. 20, 2015, the entire content of which is incorporated herein by reference.

TECHNICAL FIELD

The present disclosure relates to a catheter which has a catheter tube including a predetermined layer structure.

BACKGROUND DISCUSSION

In the related art, in order to eliminate and treat a stenosis state of a stenosis site inside a living body, a balloon catheter has been used in which a balloon is introduced into the stenosis site appearing in a lumen, a body-cavity, or the like so as to expand the stenosis site outward from the inside. For example, the balloon catheter has been used for percutaneous transluminal angioplasty (PTA) in which the stenosis site of a blood vessel is widened by the balloon so as to improve blood flow. The balloon catheter has a configuration in which the balloon is connected to a distal portion of an elongated shaft member extending in an axial direction.

The shaft member of the catheter represented by the balloon catheter has an outer tube and an inner tube arranged in a lumen of the outer tube. The shaft member is introduced into the stenosis site inside the living body by a user (operator). Accordingly, sufficient flexibility is desired in order to ensure following ability inside the living body. In addition, a guide wire is inserted into the lumen of the inner tube. Accordingly, it is desirable for a lumen surface of the inner tube to have slidable performance for operating the guide wire.

In a manufacturing process of the catheter, the catheter is generally assembled by bonding or fusing a resin. In the catheter, a material configuring a catheter distal portion (distal tip) or a member such as the balloon and the like and a material configuring the inner tube are set as the same resin material, thereby achieving satisfactory compatibility at the time of bonding or fusing and improving bonding or fusing workability.

A method has been studied in which a combination of polyolefin functioning as a material excellent in slidable performance and polyamide excellent in flexibility and suitable for a material of a balloon member and the like is used for the catheter.

JP-A-8-33705 discloses a concept relating to a balloon catheter in which at least a portion of a catheter shaft is made of polyamide configuring an outer layer and maleate polyethylene (modified polyethylene) configuring an inner layer.

SUMMARY

When bonding or fusing is performed on each member during catheter assembly work, if a catheter tube such as an inner tube and the like is colored, it is possible to ensure visibility of a bonding point or a fusing point. Therefore, using the colored catheter tube has an advantage, for example, in terms of production efficiency.

As means for coloring the catheter tube, it is conceivable to use a resin mixed with a coloring agent including a pigment, as a forming material. However, the present inventor found the following problem. If an outer layer is formed on an inner layer (the inner layer being a very slidable modified polyethylene layer) by using a mixture material obtained by adding a coloring agent having a predetermined concentration or higher to polyamide (for example, as disclosed in JP-A-8-33705 described above), visibility of the outer layer is improved. On the other hand, interlayer bonding strength becomes poor between the inner layer made of modified polyethylene and the outer layer.

Exemplary aspects of the present disclosure are made, for example, in view of the above-described circumstances. According to an exemplary aspect, provided is a catheter having a catheter tube which has excellent interlayer bonding strength between a polyamide-based resin and a modified polyolefin resin, and which can ensure visibility with a suitable color degree.

For example, the present inventor found that the above-described problem can be ameliorated or solved by an exemplary catheter. For example, the catheter has a catheter tube including a first polyamide layer, a modified polyolefin layer arranged on an inner surface of the first polyamide layer, and a second polyamide layer arranged on an outer surface of the first polyamide layer, and in which among the first polyamide layer, the second polyamide layer, and the modified polyolefin layer, only the second polyamide layer includes a coloring agent.

According to the present disclosure, it is possible to provide a catheter having a catheter tube which has excellent interlayer bonding strength between a polyamide-based resin and a modified polyolefin resin, and which can ensure visibility with a suitable color degree, when desired.

BRIEF DESCRIPTION OF THE DRAWINGS

FIGS. 1A and 1B illustrate a balloon catheter according to an exemplary embodiment.

DETAILED DESCRIPTION

According to an exemplary embodiment of the present disclosure, there is provided a catheter which has a catheter tube including a first polyamide layer, a modified polyolefin layer arranged on an inner surface of the first polyamide layer, and a second polyamide layer arranged on an outer surface of the first polyamide layer, and in which among the first polyamide layer, the second polyamide layer, and the modified polyolefin layer, only the second polyamide layer includes a coloring agent. Hereinafter, the "catheter tube including the first polyamide layer, the modified polyolefin layer arranged on the inner surface of the first polyamide layer, and the second polyamide layer arranged on the outer surface of the first polyamide layer, and in which among the first polyamide layer, the second polyamide layer, and the modified polyolefin layer, only the second polyamide layer includes the coloring agent" is referred to as a "catheter tube according to the present disclosure".

For example, the catheter tube according to the present disclosure has ensured visibility, since a pigment is mixed in the second polyamide layer of the outer layer. During a manufacturing process of the catheter, a fusing state of each member end surface is easily confirmed in carrying out fusing work when the catheter is assembled, thereby achieving satisfactory workability. For example, an exemplary catheter tube according to the present disclosure has excellent interlayer bonding strength between a polyamide-based resin and a modified polyolefin resin, despite having an outer layer including a coloring agent. This configuration can be adopted based on the following exemplary mechanism. The following exemplary mechanism is not intended to limit the technical scope of the present disclosure in any way.

For example, the coloring agent used in coloring a resin includes a pigment and a dispersant of the pigment. The pigment of the coloring agent is not compatible with the resin. The pigment is present in a state of being dispersed into a catheter tube forming material while a three-dimensional shape is maintained. Although the detailed reason is not known, it is considered that interlayer bonding strength becomes weak due to reduced interaction between a functional group of the polyamide-based resin in the polyamide layer and a polar group of the modified polyolefin resin, since the pigment is included in the layer. In a case where the polyamide layer includes a predetermined amount of the coloring agent or more, it is considered that the interlayer bonding strength becomes weak between the polyamide layer including the coloring agent and the modified polyolefin layer.

According to an exemplary aspect, an intermediate layer (first polyamide layer) is disposed between an outer layer (second polyamide layer) including the coloring agent and an inner layer (modified polyolefin layer), wherein the intermediate layer is formed of the polyamide-based resin similarly to the outer layer and wherein the intermediate layer does not include the coloring agent. For example, both the outer layer and the intermediate layer are formed of the polyamide-based resin as a raw material. For example, the outer layer and the intermediate layer are formed of the same polyamide-based resin. Accordingly, compared to the inner layer, resins for forming the outer layer and the intermediate layer are compatible with each other. It is believed that the compatibility may improve bonding strength of an interface. Furthermore, for example, the intermediate layer does not include the coloring agent. Accordingly, interaction is not reduced between the functional group of the polyamide-based resin and the polar group of the modified polyolefin layer, and the interlayer bonding strength does not become weak. It is believed that satisfactory bonding strength can be achieved even between the inner layer and the intermediate layer which respectively have different viscosities.

Hereinafter, exemplary embodiments according to the present disclosure will be described. The present disclosure is not limited to the following embodiments.

In the present specification, "X to Y" indicating a range means "X or larger and Y or smaller". In addition, unless otherwise described, measurement work for operations, physical properties, or the like is carried out under the conditions of room temperature (20° C. to 25° C.) and a relative humidity of 40% to 50%.

Figure 1A:
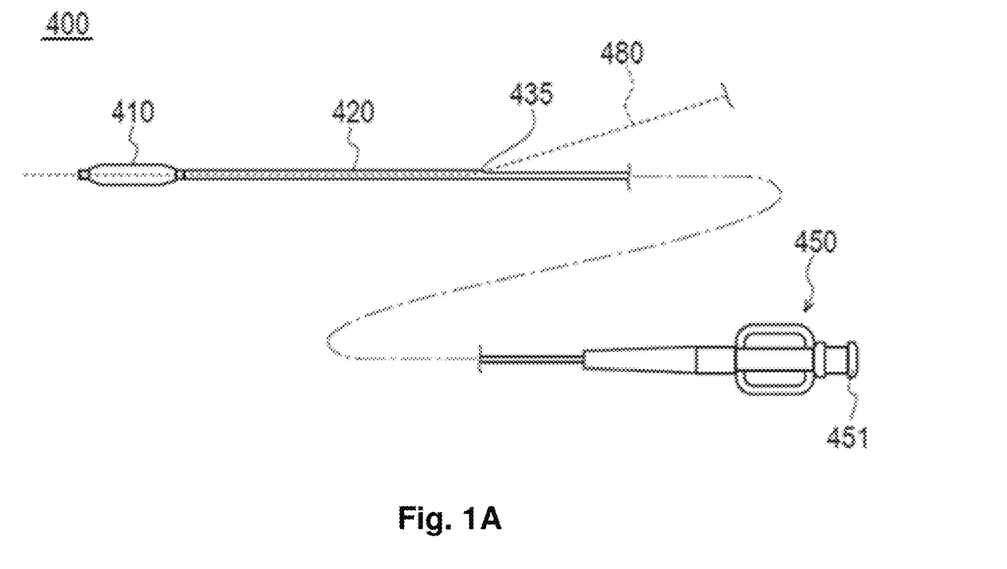
FIG. 1A illustrates a simplified overall configuration of a balloon catheter, according to an exemplary embodiment.
Figure 1B:
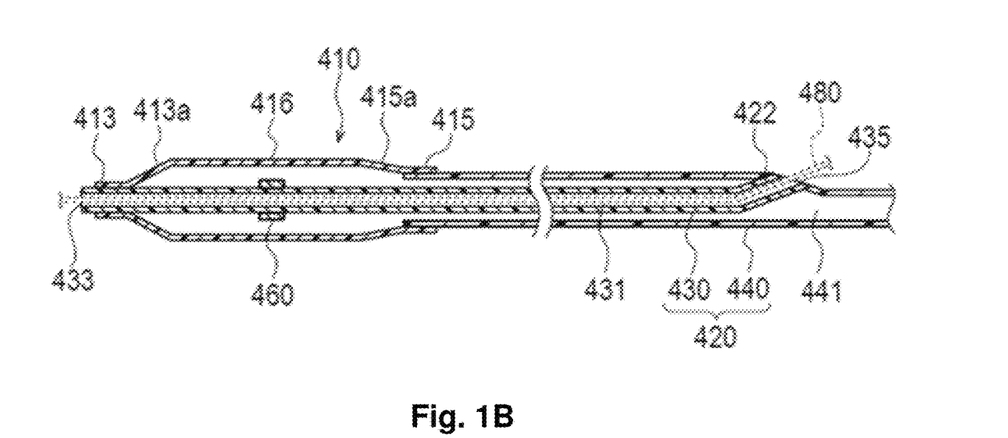
FIG. 1B is an enlarged cross-sectional view illustrating a distal portion of the balloon catheter, according to an exemplary embodiment.

According to an embodiment of the present disclosure, there is provided a catheter which has a catheter tube including a first polyamide layer, a modified polyolefin layer arranged on an inner surface of the first polyamide layer, and a second polyamide layer arranged on an outer surface of the first polyamide layer, and in which among the first polyamide layer, the second polyamide layer, and the modified polyolefin layer, only the second polyamide layer includes a coloring agent. The catheter tube according to the present disclosure can be used as an inner tube and/or an outer tube of the catheter, for example, the inner tube. Hereinafter, the present disclosure will be described in more detail with reference to an exemplary balloon catheter 400 which is a specific example of the present disclosure illustrated in FIG. 1. However, the present disclosure is not limited thereto.

The balloon catheter 400 is a medical device for widening and treating a stenosis site by inserting a shaft 420 into a living body organ and causing a balloon 410 arranged on a distal side of the shaft 420 to dilate in the stenosis site (lesion area). For example, the balloon catheter 400 is used as a PTCA balloon catheter. However, the balloon catheter 400 may be used for another treatment purpose. For example, the balloon catheter 400 may be a balloon catheter used in order to treat and improve the stenosis site formed inside the living body organ such as blood vessels in addition to coronary arteries, biliary ducts, bronchial tubes, esophagi, urethrae, other organs, and the like.

As illustrated in FIG. 1A, the balloon catheter 400 includes a flexible and elongated shaft 420, a deformable balloon 410 arranged on a distal portion side of the shaft 420 so as to dilate and deflate, and a hub 450 arranged on a proximal portion side of the shaft 420. In the description of the balloon catheter 400, a side having the balloon 410 is referred to as a distal side, and a side having the hub 450 is referred to as a proximal side.

The balloon catheter 400 can be a so-called rapid exchange type in which an opening portion 435 for guiding a guide wire 480 is disposed near the distal side of the shaft 420. However, the balloon catheter 400 can be a so-called over-the-wire type in which a guide wire lumen 431 is formed so as to extend from the distal end to the proximal end of the shaft 420.

As illustrated in FIG. 1B, the shaft 420 includes an inner tube (inner tube shaft) 430 having the guide wire lumen 431 into which the guide wire 480 is inserted, and an outer tube (outer tube shaft) 440 in which a pressurizing medium lumen 441 to which a pressurizing medium for dilating the balloon 410 is supplied is formed between an outer peripheral surface of the inner tube 430 and the outer shaft 440.

The shaft 420 is configured to have a double tube structure in which the inner tube 430 is inserted into the outer tube 440 and the inner tube 430 and the outer tube 440 are arranged so as to be concentrically aligned with each other. In an exemplary embodiment, the inner tube 430 and the outer tube 440 are not arranged so as to be concentrically aligned with each other.

As illustrated in FIG. 1B, the inner tube 430 includes two opening portions of a distal opening portion 433 formed in the distal end and a proximal opening portion 435 formed in the proximal end. The guide wire lumen 431 extends inside the inner tube 430 while communicating with the respective opening portions 433 and 435.

The inner tube 430 is configured to include a hollow tube member (catheter tube) whose proximal side is bent radially outward. A distal portion 413 of the balloon 410 is bonded to the vicinity of the distal end of the inner tube 430 in a liquid-tight and air-tight manner by using a suitable method such as fusing and the like. In addition, the vicinity of the proximal end of the inner tube 430 is bonded to an opening portion for connection 422 formed at a predetermined position of the outer tube 440, in a liquid-tight and air-tight manner. The guide wire 480 is inserted into the guide wire lumen 431 by respectively using the distal opening portion 433 disposed in the distal end of the inner tube 430 and the proximal opening portion 435 disposed in the proximal end of the inner tube 430 as an entrance and an exit.

For example, a distal tip for preventing damage to a living body organ when the distal end of the balloon catheter 400 comes into contact with the living body organ (intravascular wall or the like) can be attached to the distal end of the inner tube 430. For example, the distal tip can be configured to include a tubular member which is more flexible than the inner tube 430. The distal tip can be formed of a polyamide resin, a polyamide elastomer resin, or a blended material thereof. This can enable the inner tube 430 according to the present disclosure to have improved bonding strength between the distal tip and the inner tube 430 when the distal tip and the inner tube are fused.

An exemplary embodiment of the present disclosure employs a catheter tube according to the present disclosure as the inner tube 430. Alternatively, for example, as a material configuring the inner tube 430, it is possible to use polyolefin such as polyethylene, polypropylene, ethylene-propylene copolymer, ethylene-polyolefin vinyl acetate copolymer and the like, thermoplastic resins such as soft poly vinyl chloride, and the like, various rubber materials such as silicone rubber, latex rubber, and the like, various elastomers such as polyurethane elastomers, polyamide elastomers, polyester elastomers, and the like, or crystalline plastic materials such as polyamide, crystalline polyethylene, crystalline polypropylene, and the like. For example, it is also possible to use a material having antithrombotic properties by mixing an antithrombotic agent such as heparin, prostaglandins, urokinase, arginine derivative, and the like with these materials.

The outer tube 440 is configured to include a hollow tube member which extends from the vicinity of a proximal portion 415 of the balloon 410 to the hub 450. The proximal portion 415 of the balloon 410 is bonded to the distal end of the outer tube 440 in a liquid-tight and air-tight manner by using a suitable method such as fusing and the like.

For example, as a configuration material of the outer tube 440, it is possible to use a material which is the same as that of the inner tube 430. The outer tube 440 may be formed of a polyamide-based resin (to be described later). In addition, a portion in contact with the blood in the outer tube 440 (for example, an outer surface of the outer tube 440) can be coated with a material having antithrombotic properties. The portion can be formed of a resin mixed with an antithrombotic agent.

As a forming material of the balloon 410, it is exemplary to use an elastic material. For example, it is possible to use thermoplastic elastomers such as vinyl chloride, polyurethane elastomers, polystyrene elastomers, styrene-ethylene-butylene-styrene copolymer (SEBS), styrene-ethylene-propylene-styrene copolymer (SEPS), and the like, thermoplastic resins such as PET and the like, thermosetting resins such as rubber, silicone elastomers, and the like, polyamide resins, polyamide elastomer resins, or blended materials thereof. In addition, the balloon 410 may be a multi-layer balloon having two or more layers. The balloon 410 can be formed of a polyamide resin, a polyamide elastomer resin, or a blended material thereof. This can improve bonding strength between the balloon and the inner tube when the balloon and the inner tube are fused, for example, in a case where the catheter tube according to the present disclosure is used as the inner tube.

As illustrated in FIG. 1A, the hub 450 includes a connection portion 451 which can be connected to a supply device (not illustrated) such as an in-deflator for supplying the pressurizing medium in a liquid-tight and air-tight manner. For example, the connection portion 451 of the hub 450 can be configured to include a suitable Luer tape or the like having a configuration in which a fluid tube or the like can be connected and separated.

The pressurizing medium (for example, a physiological saline solution, a contrast agent, or the like) used in dilating the balloon 410 can be caused to flow into the shaft 420 via the connection portion 451 of the hub 450. The pressurizing medium is supplied to the balloon 410 by way of the pressurizing medium lumen 441.

As illustrated in FIG. 1B, the balloon 410 includes an effectively dilatable portion (pressurizing portion) 416 which widens a stenosis site by being dilated and deformed, a distal side tapering portion 413a linked to a distal side of the effectively dilatable portion 416, and a proximal side tapering portion 415a linked to a proximal side of the effectively dilatable portion 416. A distal portion 413 located on a distal side of the distal side tapering portion 413a is fixed to the outer surface of the inner tube 430, and a proximal portion 415 located on a proximal side of the proximal side tapering portion 415a is fixed to the outer surface of the outer tube 440. An X-ray imaging marker 460 indicating a central portion of the effectively dilatable portion 416 is disposed in the center of the effectively dilatable portion 416 in the inner tube 430. In addition, the X-ray imaging marker 460 may be disposed in a portion located in both ends of the effectively dilatable portion 416 in the inner tube 430 so as to indicate both ends of the effectively dilatable portion 416.

The catheter tube according to the present disclosure is provided with visibility. Therefore, since the catheter tube according to the present disclosure can be used as the inner tube of the catheter, a bonding state between members is easily visible when the outer tube or the balloon and the inner tube are bonded or fused. For example, in a case of the balloon catheter 400, the catheter tube according to the present disclosure is used, for example, as the inner tube 430. Accordingly, visibility is ensured in carrying out bonding work or fusing work for the distal portion 413 of the balloon 410, or the opening portion for connection 422 to the outer tube 440.

According to an exemplary embodiment of the present disclosure, the catheter tube according to the present disclosure is used as the inner tube of the balloon catheter. That is, according to an exemplary embodiment of the present disclosure, there is provided a balloon catheter including an outer tube that has a lumen, an inner tube that is arranged in the lumen of the outer tube, and a balloon that is fixed to a distal side of the inner tube and a distal side of the outer tube. The balloon includes, for example, a polyamide-based resin. For example, the inner tube includes a first polyamide layer, a modified polyolefin layer arranged on an inner surface of the first polyamide layer, and a second polyamide layer arranged on an outer surface of the first polyamide layer. Among the first polyamide layer, the second polyamide layer, and the modified polyolefin layer, only the second polyamide layer includes a pigment. As the polyamide-based resin included in the balloon, it is possible to employ those which are described in the first polyamide layer. The polyamide-based resin which is the forming material of the balloon may be the same as or different from the polyamide-based resin which is the forming material of the first polyamide layer or the second polyamide layer. According to an exemplary embodiment of the present disclosure, the balloon is formed of the polyamide-based resin.

Figure 2:
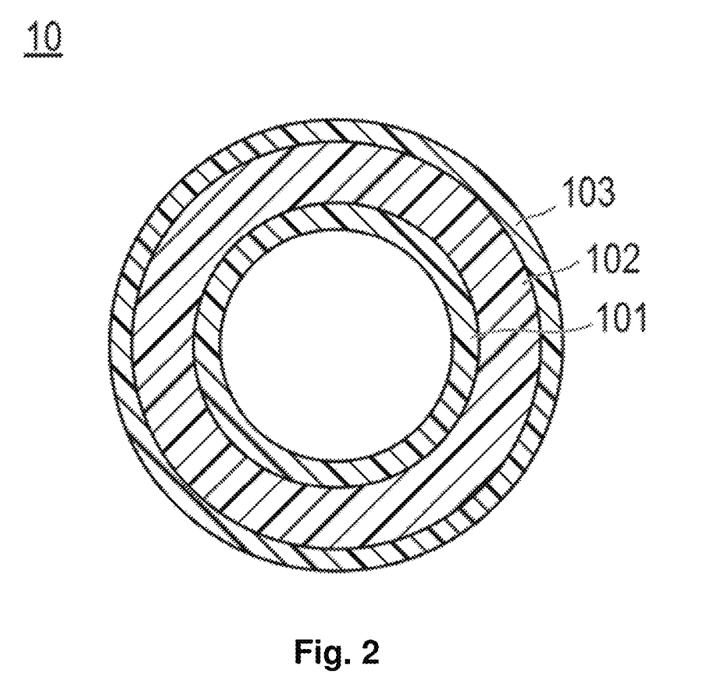
FIG. 2 illustrates a layer configuration (axially perpendicular cross-sectional view) which is an example of a catheter tube, according to an exemplary embodiment.

FIG. 2 illustrates a layer configuration (axially perpendicular cross-sectional view) which is a specific example of the catheter tube according to an exemplary embodiment of the present disclosure. However, the present disclosure is not limited thereto. In FIG. 2, a shape of the axially perpendicular cross section of the catheter tube is circular, but may be polygonal or the like. The cross-sectional shape is not limited in an exemplary embodiment. In FIG. 2, a catheter tube 10 is configured to include a modified polyolefin layer (inner layer) 101, a first polyamide layer (intermediate layer) 102 formed on an outer surface of the modified polyolefin layer 101, and a second polyamide layer (outer layer) 103 formed on an outer surface of the first polyamide layer 102. The catheter tube 10 can have the first polyamide layer (intermediate layer) 102 which is thicker than the second polyamide layer (outer layer) 103. The first polyamide layer (intermediate layer) 102 which does not include a coloring agent can be thicker than the second polyamide layer (outer layer) 103 which includes the coloring agent. For example, in a case where the balloon catheter employs the catheter tube 10 as the inner tube, when a distal tip and the inner tube are brought into contact with and bonded to each other, it is possible to improve bonding strength between a polyamide resin of the distal tip and a resin member including a polyamide elastomer resin or a blended material thereof.

The catheter tube 10 according to the present disclosure may optionally have another layer such as one or more of the following layers in addition to the modified polyolefin layer (inner layer) 101, the first polyamide layer (intermediate layer) 102, and the second polyamide layer (outer layer) 103. For example, in order to further improve slidable performance of the guide wire, the catheter tube according to the present disclosure may further include a fluorine-based resin layer (not illustrated) formed of fluorine-based resins such as polytetrafluoroethylene, polyvinylidene fluoride, ethylene-tetrafluoroethylene, perfluoroalkoxy resin, and the like, on the inner surface of the polyolefin layer (inner layer) 101. In addition, if desired, a reinforcing layer (not illustrated) in which a linear member made of a metal wire or a non-metal wire is braided or wound in a spiral shape may be disposed between the polyolefin layer (inner layer) 101 and the first polyamide layer 102 or between the first polyamide layer 102 and the second polyamide layer 103.

An outer diameter of the catheter tube according to the present disclosure may be appropriately set depending on the intended use, and is not particularly limited. For example, in a case of being employed as the inner tube of the catheter tube 10, the outer diameter can be 300 μm to 800 μm, for example, 500 μm to 600 μm. In addition, inner diameter of the catheter tube is also not particularly limited. For example, in a case of being employed as the inner tube of the catheter tube 10, the inner diameter can be 250 μm to 600 μm, for example, 400 μm to 500 μm.

For example, a thickness (thickness of the entirety of layers including the polyolefin layer, the first polyamide layer, the second polyamide layer, and other optionally set layers) of the catheter tube according to the present disclosure can be 100 μm to 200 μm, for example, 120 μm to 170 μm.

Hereinafter, each layer of the polyolefin layer (inner layer), the first polyamide layer (intermediate layer), and the second polyamide layer (outer layer) will be described in more detail.

According to an exemplary embodiment of the present disclosure, the modified polyolefin layer (inner layer) is formed of a modified polyolefin resin. Since the inner layer is the modified polyolefin layer, slidable performance is improved when the guide wire is inserted.

For example, the modified polyolefin resin which can be suitably used for the modified polyolefin layer can include polyethylene, polypropylene, α-olefin (such as 1-butene, 1-hexene, 4-methyl-1-pentene, 1-octene, 1-decene, and the like) copolymer, ethylene-propylene copolymer, cyclo-olefin polymer (for example, copolymer of cyclic olefin such as norbornene, cyclobutene, cyclopentene, and the like), cyclo-olefin copolymer (for example, a copolymer of cyclic olefin and chain olefin such as polyethylene, and the like, or copolymer of cyclic olefin and diene such as 1,4-hexadiene, and the like), mixtures thereof which are a material having pendant including a polar group or a reactive group; ethylene-vinyl acetate copolymer, or the like. In a case of the copolymer, a structure thereof is not particularly limited. Any one may be selected from random copolymer, alternating copolymer, periodic copolymer, and block copolymer.

Among these, as the modified polyolefin resin, in view of slidable performance of the modified polyolefin layer, it is exemplary to select modified polyethylene (high density polyethylene, low density polyethylene, low density polyethylene having a straight-chain shape, and the like), or modified polypropylene, for example, modified polyethylene, for example, modified high density polyethylene.

For example, the modified polyolefin resin is a polyolefin resin having pendant including a polar group such as a carboxyl group, a carboxylic anhydride group, a hydroxyl group, an alkoxy group, an imido group, an acryloyl group, a methacryloyl group, a silanyl group and/or a silanol group, and the like or a reactive group. The modified polyolefin is used, for example, so as to improve bonding strength with the first polyamide layer, compared to a case of using a low polarity polyolefin resin.

Examples of the modified polyolefin resin may include one that contains a unit derived from a monomer having a polar group or a reactive group and a unit derived from chain or cyclic olefin, for example, at a molar ratio of 1:99 to 50:50, like ethylene-vinyl acetate copolymer. For example, the modified polyolefin resin may be those which are modified by grafting the polar group or the reactive group onto a main chain of polyolefin. In grafting the polyolefin resin, an unsaturated carboxylic acid compound, an unsaturated silane compound, or the like is grafted onto and copolymerized with a side chain of the polyolefin by using a suitable method in the related art. For example, the grafted chain to be added can include a carboxyl group, a hydroxyalkyl group, and an alkoxy group which have a straight chain or a branched chain having 1 to 6 carbon atoms; a carboxylic acid anhydride group having 5 to 10 carbon atoms; an imide group; an acryloyl group; a methacryloyl group; a silanyl group; and a silanol group. The silanyl group is represented by —Si($X^1$)($X^2$)($X^3$) (in the formula, $X^1$, $X^2$, and $X^3$ are respectively and independently alkyl groups which have a straight chain or a branched chain having 1 to 6 carbon atoms). The above-described pendant may be further substituted with an alkyl group having 1 to 2 carbon atoms, a hydroxyl group, the above-described carboxyl group, a hydroxyalkyl group and/or an alkoxy group. For example, grafting the polyolefin resin can be performed by means of a solvent method of reacting in a solvent while optionally using a catalyst, a kneading method of reacting in a molten state obtained by using a kneading extruder, or the like.

For example, the unsaturated carboxylic acid compound used for grafting can include unsaturated monocarboxylic acid and a derivative thereof such as acrylic acid, methacrylic acid, methoxyethyl acrylate, methoxyethyl methacrylate, hydroxyethyl acrylate, hydroxypropyl acrylate, and the like; unsaturated dicarboxylic acid and a derivative thereof such as maleic acid, tetrahydrophthalic acid, itaconic acid, citraconic acid, crotonic acid, isocrotonic acid, maleimide, maleic anhydride, citraconic anhydride, monomethyl maleate, and the like. In addition, the unsaturated silane compound can include an olefin-based unsaturated silane compound such as vinyl trimethoxysilane, vinyl triethoxtsilane, and the like.

Among the above-described materials, as the unsaturated carboxylic acid compound, it is exemplary to use maleic acid or maleic anhydride acid from a viewpoint that bonding strength with the first polyamide layer can be further improved since the polyolefin resin becomes hydrophilic. That is, it is exemplary to use a maleated polyolefin resin such as maleated polyethylene, maleated polypropylene, and the like, for example, maleated polyethylene. According to an embodiment of the present disclosure, there is provided a catheter in which a resin forming the modified polyolefin layer is the maleated polyethylene. According to another exemplary embodiment of the present disclosure, there is provided a balloon catheter in which the resin forming the modified polyolefin layer is the maleated polyethylene. For example, the resin forming the modified polyolefin layer is maleated high density polyethylene.

A terminal of the modified polyolefin resin may be those which have the above-described unsaturated carboxylic acid compound added thereto. The above-described modified polyolefin resin may be used alone. Alternatively, two or more types may be used in combination.

As the above-described modified polyolefin resin, a commercially available product may be used. For example, the modified polyolefin resin can include MODIC (registered trademark) series (H511, HSO3, L502, L533, L504, M142, M502, M512, M545, A543, and A515), LINKLON (registered trademark) series (hitherto, Mitsubishi Chemical Corporation), ADMER (registered trademark) series (Mitsui Chemicals, Inc.), HIMILAN (registered trademark) series (Mitsui DuPont Polychemicals Co., Ltd.), and the like.

A weight-average molecular weight of the modified polyolefin resin can be 1,000 to 10,000,000. According to the present disclosure, the "weight-average molecular weight" of the polyolefin resin employs a value measured by gel permeation chromatography (GPC).

A layer thickness of the polyolefin layer can be 1 μm to 100 μm, for example, 5 μm to 50 μm. This can enable the inner surface of the catheter tube to ensure sufficient slidable performance for operating the guide wire.

According to an exemplary embodiment of the present disclosure, the first polyamide layer (intermediate layer) is formed of a polyamide-based resin. The polyamide-based resin is flexible and strong, and can have an advantage in that an elastic region is larger than that in a case of using polyester such as polyethylene terephthalate. In addition, the intermediate layer can be formed by using the same polyamide-based resin as that of the second polyamide layer (outer layer). For example, it is possible to prevent the uneven layer thickness of the outer layer/intermediate layer which is caused by different viscosity of the forming materials during co-extrusion. The "polyamide-based resin" means a polyamide resin, a polyamide elastomer resin, and/or a blended resin thereof.

The polyamide-based resin which can be suitably used for the first polyamide layer is not particularly limited as long as the main chain has acid amide bonds (—CO—NH—). The polyamide-based resin can be manufactured in the presence of a suitable catalyst by lactam of the cyclic structure or polymerization of amino acid, and alternatively, by condensation polymerization of dicarboxylic acid and diamine.

A monomer which can be polymerized alone includes ε-caprolactam, undecanoic lactam, lauryllactam, aminocaproic acid, 7-amino hepatoic acid, 11-aminoundecanoic acid, 12-aminoundecanoic acid, 9-aminononanoic acid, pieridone, and the like.

In addition, dicarboxylic acid in a case where dicarboxylic acid and diamine are subjected to condensation polymerization can include adipic acid, sebacic acid, dodecane dicarboxylic acid, glutaric acid, terephthalic acid, 2-methyl terephthalic acid, isophthalic acid, naphthalene dicarboxylic acid, and the like. Diamine can include tetramethylene diamine, hexamethylene diamine, nonamethylene diamine, decamethylene diamine, undecamethylene diamine, dodecamethylene diamine, paraphenylene diamine, meta-phenylenediamine, and the like.

As the polyamide-based resin, a polyamide elastomer resin may be used. For example, the polyamide elastomer resin can include a block copolymer of polyamide (hard segment) and polyether (soft segment). For example, the polyamide elastomer resin includes a block copolymer of nylon 11 and polytetramethylene glycol, a block copolymer of nylon 12 and polytetramethylene glycol, and the like.

As the polyamide-based resin, it is exemplary to use those which do not have a segment other than polyamide. For example, nylon 4, 6, 7, 8, 11, 12, 6.6, 6.9, 6.10, 6.11, 6.12, 6T, 6/6.6, 6/12, 6/6T, 6T/6I, and the like are used. As the polyamide-based resin, it is exemplary to particularly use nylon 11 and nylon 12 among the above-described materials.

A terminal of the polyamide-based resin may be sealed with a carboxyl group, an amino group, and the like. The above-described polyamide-based resin may be used alone. Alternatively, two or more types may be used in combination.

As the above-described polyamide-based resin, a commercially available product may be used. For example, the polyamide-based resin can include DAIAMID (registered trademark) series (L1640, L1840, L1940, L1940W, L2140, L2140W, L2121, and the like), VESTAMID (registered trademark) series (hitherto, Daicel-Evonik Ltd.), PEBAX (registered trademark) series (Arkema Yoshitomi, LTD.), AMILAN (registered trademark) series (Toray Industries, Inc.), LEONA (registered trademark) series (Asahi Kasei Fibers Corporation), UBE NYLON (registered trademark) series (Ube Industries, Ltd.), LENNY (registered trademark) series (Mitsubishi Engineering-Plastics Corporation), ZYTEL (registered trademark) series (DuPont Co., Ltd.), GRILAMID (registered trademark), GRILL FLEX (registered trademark) (hitherto, EMS Chemie Japan Ltd.), RILSAMID (registered trademark) (Arkema Yoshitomi, LTD.), and the like. In addition, the polyamide-based resin of the above-described commercially available product may be used alone, or may be used by blending two or more polyamide-based resins.

The weight-average molecular weight of the polyamide-based resin can be 10,000 to 500,000, for example, 15,000 to 300,000. According to the present disclosure, the "weight-average molecular weight" of the polyamide-based resin can be measured by using the method described above in the polyolefin resin.

The layer thickness of the first polyamide layer (radial thickness of the inner tube in the first polyamide layer) can be thicker than the layer thickness of the second polyamide layer to be described later (radial thickness of the inner tube in the second polyamide layer). The first polyamide layer which does not include the coloring agent can be thicker than the second polyamide layer which includes the coloring agent. For example, in a case where the catheter tube is employed for the inner tube of the balloon catheter, it is possible to improve bonding strength with the distal tip or the balloon. According to an exemplary embodiment of the present disclosure, there is provided a balloon catheter in which the layer thickness of the first polyamide layer is thicker than the layer thickness of the second polyamide layer. For example, the layer thickness of the first polyamide layer can be 60 μm to 140 μm, for example, 70 μm to 120 μm.

According to an exemplary embodiment of the present disclosure, the second polyamide layer (outer layer) is formed of the polyamide-based resin and the coloring agent. In order to form the second polyamide layer including the polyamide-based resin and the coloring agent, a material obtained by mixing the polyamide-based resin and the coloring agent with each other at any desired ratio may be used for co-extrusion molding of the catheter tube as a raw material of the second polyamide layer. For example, the polyolefin layer (inner layer) 101 and the first polyamide layer (intermediate layer) 102 may include small quantities of a coloring agent. For example, an amount of a coloring agent present in the second polyamide layer is greater than an amount of a coloring agent present in the first polyamide layer. For example, an amount of a coloring agent present in the second polyamide layer is greater than an amount of a coloring agent present in the modified polyolefin layer.

Since the polyamide-based resin is flexible and strong, the polyamide-based resin can be used as a material of the outer tube or the balloon of the catheter. The outer layer of the inner tube serving as the catheter tube can be formed by using the polyamide-based resin which can also be used for other members. For example, members are allowed to have improved compatibility when the members are fused, and it is possible to effectively prevent breakage of the catheter. In addition, the polyamide-based resin is employed as a resin forming the outer layer of the inner tube. Accordingly, even if a lumen is greatly bent, it is possible to smoothly insert the catheter into the lumen without any kink.

With regard to the polyamide-based resin and the molecular weight which can be suitably used for the second polyamide layer, for example, the description with regard to the above-described first polyamide layer is similarly applied. From a viewpoint of bonding strength, it is exemplary to use the same polyamide-based resin for the first polyamide layer and the second polyamide layer.

The coloring agent included in the second polyamide layer can be appropriately used by selecting various colors such as black, red, green, blue, yellow, purple, white, and the like, depending on a desired color tone. For example, the coloring agent is used in order to discriminate a colored member from other members. For example, in a case where the catheter tube according to the present disclosure is employed as the inner tube, it is exemplary to use a pigment having a color or brightness which is different from that of a bonding portion or a fusing portion of other members for bonding or fusing. For example, in a case where the catheter tube according to the present disclosure is employed as the inner tube, an example may be adopted in which a black coloring agent is used for the catheter tube in relation to a white outer tube.

For example, the coloring agent includes a pigment used in coloring resins and a dispersant for dispersing the pigment in the resins. As the pigment, an inorganic pigment and an organic pigment which are known in the related art can be used. Although not particularly limited, for example, the inorganic pigment can include carbon black, titanium oxide, barium sulfate, iron oxide (black iron oxide, yellow iron oxide, and red iron oxide), chromium oxide, ultramarine (ultramarine-based blue, ultramarine-based violet), nickel titanium yellow, Prussian blue, Milori blue, cobalt blue, Viridian, molybdenum red, and the like. In addition, for example, the organic pigment can include pigments or the like of quinacridone system (for example, quinacridone-based red), perylene system (for example, perylene red), anthraquinone system (for example, anthraquinone-based yellow), azo system (for example, condensed azo-based yellow organic pigment), phthalocyanine system (for example, halogenated phthalocyanine such as copper phthalocyanine, high chloride phthalocyanine, and the like). The above-described pigment may be used alone. Alternatively, two or more types may be used in combination.

From a viewpoint of heat resistance during extrusion molding, the inorganic pigment can be used.

The coloring agent used in forming the second polyamide layer can have the dispersant such as a surfactant and the like in addition to the pigment. In addition, the coloring agent may include an additive such as a stabilizer and the like in addition to the pigment and the dispersant. In a case of using the coloring agent, the weight ratio of the coloring agent to other materials such as the polyamide-based resin and the like may be appropriately adjusted so that the pigment content included in the second polyamide layer falls within the above-described range. The pigment content included in the coloring agent is, for example, 25 wt % or greater from a viewpoint of coloring the resin.

By use of the second polyamide layer including the coloring agent, for example, it is possible to improve visibility of the catheter tube. For example, from a viewpoint of improving the visibility and interlayer bonding strength, for example, the pigment content included in the second polyamide layer is 0.3 wt % or greater with respect to the entire solid content of the second polyamide layer, for example, 0.6 wt % or greater. In addition, from a viewpoint of stably dispersing the pigment in the resin, the pigment content is, for example, 50 wt % or smaller with respect to the entire solid content of the second polyamide layer, for example, 20 wt % or smaller. The pigment content included in the second polyamide layer can be set to 0.6 wt % or greater. For example, even if the layer thickness of the second polyamide layer is reduced to approximately 20 μm, it is possible to ensure satisfactory visibility. That is, according to an exemplary embodiment of the present disclosure, there is provided a catheter in which the coloring agent includes the pigment, and in which the second polyamide layer includes the pigment content of 0.6 wt % or greater with respect to the entire solid content of the second polyamide layer. According to another exemplary embodiment of the present disclosure, there is provided a balloon catheter in which the coloring agent includes the pigment, and in which the second polyamide layer includes the pigment having the pigment content of 0.6 wt % or greater with respect to the entire solid content of the second polyamide layer. In addition, the pigment content included in the second polyamide layer can be set to 50 wt % or smaller. For example, it is possible to stably disperse the pigment in the second polyamide layer. According to an exemplary embodiment of the present disclosure, provided are a catheter and a balloon catheter in which the second polyamide layer includes the pigment content of 0.3 wt % to 20 wt % with respect to the entire solid content of the second polyamide layer, for example, the pigment content of 0.6 wt % to 10 wt %, for example, the pigment content of 0.6 wt % to 5 wt %.

In addition, from a viewpoint of coloring the resin, the coloring agent can include the pigment content of 25 wt % or greater with respect to the entire solid content of the coloring agent, for example, the pigment content of 40 wt % or greater. The amount of the coloring agent added to the second polyamide layer may be appropriately set according to the pigment content included in the coloring agent or a color tone of the layer. For example, in a case where the pigment amount of 40 wt % or greater is included in the coloring agent, the amount of the coloring agent can be set to 0.75 wt % or greater with respect to the entire solid content of the second polyamide layer, for example, 1.5 wt % or greater. According to an exemplary embodiment of the present disclosure, there is provided a catheter in which the coloring agent includes the pigment content of 40 wt % or greater with respect to the entire solid content of the coloring agent, and in which the second polyamide layer includes the coloring agent of 1.5 wt % or greater with respect to the entire solid content of the second polyamide layer. According to another exemplary embodiment of the present disclosure, there is provided a balloon catheter in which the coloring agent includes the pigment content of 40 wt % or greater with respect to the entire solid content of the coloring agent, and in which the second polyamide layer includes the coloring agent of 1.5 wt % or greater with respect to the entire solid content of the second polyamide layer. In addition, from a viewpoint of stably dispersing the pigment in the resin, the amount of the coloring agent can be 50 wt % or smaller with respect to the entire solid content of the second polyamide layer, for example, 25 wt % or smaller.

As the dispersant used for the coloring agent, those which are known in the related art can be employed. For example, the dispersant can include surfactants such as an anionic surfactant (for example, alkyl sulfate, fatty acid salt, and the like), a cationic surface active agent (aliphatic amine salt, quaternary ammonium salt, and the like), an amphoteric surfactant, a nonionic surfactant (fatty acid ester, polyethylene glycol, and the like); and polymer dispersants such as polycarboxylic acid and amine salt thereof, polycarboxylic acid ester, polyurethane, modified polyacrylate, polyester amide and amine salt thereof, alginic acid, polyvinyl alcohol, carboxymethyl cellulose, and the like.

For example, the coloring agent includes the pigment of 25 wt % to 90 wt % (in a case of using multiple pigments, a total amount thereof) and the dispersant of 75 wt % to 10 wt % (in a case of using multiple dispersants, a total amount thereof), and the total amount of the pigment and the dispersant is 100 wt %. The coloring agent having this composition can be used to improve or ensure visibility and satisfactorily dispersion of the pigment in the layer. For example, the coloring agent used according to the present disclosure includes the pigment of 40 wt % to 75 wt % (in a case of using multiple pigments, a total amount thereof) and the dispersant of 60 wt % to 25 wt % (in a case of using multiple dispersants, a total amount thereof), and the total amount of the pigment and the dispersant is 100 wt %.

According to an exemplary embodiment of the present disclosure, the second polyamide layer includes the dispersant of 0.1 wt % or greater with respect to the entire solid content of the second polyamide layer.

According to an exemplary embodiment of the present disclosure, the second polyamide layer includes the polyamide-based resin of 60 wt % to 99.6 wt % (solid basis), the pigment of 0.3 wt % to 20 wt % (solid basis), and the dispersant of 0.1 wt % to 20 wt % (solid basis).

The layer thickness of the second polyamide layer can be thinner than the layer thickness of the first polyamide layer. For example, a ratio between the first polyamide layer and the second polyamide layer is 100:1 to 2:1 (layer thickness of the first polyamide layer:layer thickness of the second polyamide layer), for example, 3:1 to 8:1. The layer thickness of the second polyamide layer can be 10 μm to 40 μm, for example, 15 μm to 30 μm. The layer thickness of the second polyamide layer can be set to 15 μm or greater. Accordingly, visibility can be ensured. The layer thickness of the second polyamide layer can be set to 30 μm or smaller. Accordingly, it is possible to provide the catheter tube having a narrow tube diameter.

For example, the catheter tube according to the present disclosure can be formed through co-extrusion molding by using fine powder of a modified polyolefin resin, fine powder of the polyamide-based resin, dispersion for coating, and the like (pigment further included in the coloring agent for the second polyamide layer) as a raw material. Production conditions during the extrusion molding can be optionally set by those skilled in the art, for example, and one exemplary condition is a melting temperature of 100° C. to 250° C.

An exemplary advantageous effect will be described with reference to the following examples and comparative examples. However, the technical scope of the present disclosure is not limited only to the following embodiments. An operation is performed at room temperature (25° C.) unless otherwise described.

EXAMPLES

A tube 1 (ϕ0.43×0.46×0.55×0.57 mm) was obtained through co-extrusion molding of a triple-layer tube which has the inner layer (modified polyolefin layer), the intermediate layer (first polyamide layer), and the outer layer (second polyamide layer). The following products were used as a material of each layer:

Modified polyolefin layer (layer thickness 30 μm): maleated high density polyethylene (MODIC H503 (Mitsubishi Chemical Corporation))

First polyamide layer (layer thickness 90 μm): Nylon 12 (DIAMID L1940W (Daicel-Evonik Ltd.))

Second polyamide layer (layer thickness 20 μm): Nylon 12 (DIAMID L1940W (Daicel-Evonik Ltd.)), including coloring agent (the coloring agent including: carbon black (black pigment) of 25 wt %, titanium oxide (white pigment) of 25 wt %, and an anionic surfactant (dispersant) of 50 wt %) in an amount of 1.0 wt % with respect to the entire solid content of the second polyamide layer. That is, the pigment in an amount of 0.5 wt % is included with respect to the entire solid content of the second polyamide layer.

A tube 2 was obtained through co-extrusion molding of the triple-layer tube, similarly to Embodiment 1, except that the amount of the coloring agent included in the second polyamide layer is set to 2.0 wt % with respect to the entire solid content of the second polyamide layer (pigment in an amount of 1.0 wt % with respect to the entire solid content of the second polyamide layer).

A tube 3 was obtained through co-extrusion molding of the triple-layer tube, similarly to Embodiment 1, except that the amount of the coloring agent included in the second polyamide layer is set to 3.0 wt % with respect to the entire solid content of the second polyamide layer (pigment in an amount of 1.5 wt % with respect to the entire solid content of the second polyamide layer).

A tube 4 was obtained through co-extrusion molding of the triple-layer tube, similarly to Embodiment 1, except that the amount of the coloring agent included in the second polyamide layer is set to 5.0 wt % with respect to the entire solid content of the second polyamide layer (pigment in an amount of 2.5 wt % with respect to the entire solid content of the second polyamide layer).

Comparative Example 1

A comparative tube 1 (φ0.43×0.46×0.57 mm) was obtained through co-extrusion molding of a double-layer tube which has the inner layer (modified polyolefin layer), and the outer layer (polyamide layer). The following products are used as a material of each layer;

Modified polyolefin layer (layer thickness 30 μm): maleated high density polyethylene (MODIC H503 (Mitsubishi Chemical Corporation))

Polyamide layer (layer thickness 110 μm): Nylon 12 (DIAMID L1940W (Daicel-Evonik Ltd.)), including a coloring agent (the coloring agent including carbon black (black pigment) of 25 wt %, titanium oxide (white pigment) of 25 wt %, and an anionic surfactant (dispersant) of 50 wt %) in an amount of 1.0 wt % with respect to the entire solid content of the polyamide layer. That is, the pigment in an amount of 0.5 wt % is included with respect to the entire solid content of the polyamide layer.

Comparative Example 2

A comparative tube 2 was obtained through co-extrusion molding of the double-layer tube, similarly to Comparative Example 1, except that the amount of the coloring agent included in the polyamide layer is set to 0.5 wt % with respect to the entire solid content of the polyamide layer (pigment in an amount of 0.25 wt % with respect to the entire solid content of the polyamide layer).

Comparative Example 3

A comparative tube 3 was obtained through co-extrusion molding of the double-layer tube, similarly to Comparative Example 1, except that the amount of the coloring agent included in the polyamide layer is set to 0.3 wt % with respect to the entire solid content of the polyamide layer (pigment in an amount of 0.15 wt % with respect to the entire solid content of the polyamide layer).

Comparative Example 4

A comparative tube 4 was obtained through co-extrusion molding of the double-layer tube, similarly to Comparative Example 1, except that the amount of the coloring agent included in the polyamide layer is set to 0.2 wt % with respect to the entire solid content of the polyamide layer (pigment in an amount of 0.1 wt % with respect to the entire solid content of the polyamide layer).

Comparative Example 5

A comparative tube 5 was obtained through co-extrusion molding of the double-layer tube, similarly to Comparative Example 1, except that the amount of the coloring agent included in the polyamide layer is set to 0.1 wt % with respect to the entire solid content of the polyamide layer (pigment in an amount of 0.05 wt % with respect to the entire solid content of the polyamide layer).

The catheter tube obtained according to the above-described embodiments and comparative examples was cut to have a length of 10 cm, and the tube was bent at an angle of 180° in the axially central portion. After bending was repeatedly carried out four times, it was visually confirmed whether or not interlayer separation was present in the bent portion.

O: The interlayer separation was not observed in the bent portion.

x: The interlayer separation was observed in the bent portion.

Visibility of the catheter tube was evaluated by using the catheter tube obtained according to the above-described embodiments and comparative examples.

O: The catheter tube is colored in black (Munsell value: 5 or lower). When the guide wire is inserted into the lumen of the catheter tube, the guide wire arranged in the lumen of the catheter is hardly visible.

Δ: When the guide wire is inserted into the lumen of the catheter tube, the guide wire arranged in the lumen of the catheter is visible, but the color of the catheter tube can be confirmed (Munsell value: 6 to 8).

x: There is a small difference between the colored and non-colored catheter tubes, and the color of the catheter tube can hardly be confirmed (Munsell value: 9 to 10).

TABLE 1

| | Coloring Agent (wt %) of Second Polyamide Layer (Tubes 1 to 4) or Polyamide Layer (Comparative Tubes 1 to 4) | Pigment (wt %) of Second Polyamide Layer (Tubes 1 to 4) or Polyamide Layer (Comparative Tubes 1 to 4) | Interlayer Bonding Strength | Visibility |
|---|---|---|---|---|
| Tube 1 | 1.0 | 0.5 | O | Δ |
| Tube 2 | 2.0 | 1.0 | O | O |
| Tube 3 | 3.0 | 1.5 | O | O |
| Tube 4 | 5.0 | 2.5 | O | O |
| Comparative Tube 1 | 1.0 | 0.5 | X | O |
| Comparative tube 2 | 0.5 | 0.25 | X | O |
| Comparative Tube 3 | 0.3 | 0.15 | X | X |
| Comparative Tube 4 | 0.2 | 0.1 | O | X |
| Comparative Tube 5 | 0.1 | 0.05 | O | X |

As illustrated in the above table, in the catheter tube according to the present disclosure, the interlayer separation was not observed even in a case where a large amount of the coloring agent is included in the forming material of the catheter tube.

In the catheter tube according to the present disclosure, the pigment included in the second polyamide layer was set to 0.6 wt % or greater. In this manner, it was confirmed that the catheter tube is observed with particularly high visibility. This improves workability for bonding or fusing. The layer thickness (20 μm) of the outer layer including the pigment in the tubes 1 to 4 is thinner than the layer thickness of the outer layer (110 μm) including the pigment in the comparative tubes 1 to 5. If the pigment including layer is thinned, the visibility tends to be poor. However, the catheter tube according to the present disclosure can increase the pigment content included in the outer layer. Therefore, the outer layer can be thinned.

The detailed description above describes, for example, exemplary catheters. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

REFERENCE NUMERALS IN THE DRAWINGS 10 catheter tube
101 polyolefin layer
102 first polyamide layer
103 second polyamide layer
400 balloon catheter
410 balloon
413 distal portion of balloon
413a distal side tapering portion
415 proximal portion
415a proximal side tapering portion
416 effectively dilatable portion
420 shaft
422 opening portion for connection
430 inner tube
431 guide wire lumen
433 distal opening portion
435 proximal opening portion
440 outer tube
441 pressurizing medium lumen
450 hub
451 connection portion
460 X-ray imaging marker
480 guide wire

What is claimed is:

1. A catheter, comprising:
a catheter tube,
wherein the catheter tube includes a first polyamide layer, a modified polyolefin layer arranged on an inner surface of the first polyamide layer, and a second polyamide layer arranged on an outer surface of the first polyamide layer, and
wherein among the first polyamide layer, the second polyamide layer, and the modified polyolefin layer, only the second polyamide layer includes a coloring agent.

2. The catheter according to claim 1, wherein the coloring agent includes a pigment, and
wherein the second polyamide layer includes the pigment in an amount of 0.6 wt % or greater with respect to an entire solid content of the second polyamide layer.

3. The catheter according to claim 1, wherein the coloring agent includes a pigment in an amount of 40 wt % or greater with respect to an entire solid content of the coloring agent, and
wherein the second polyamide layer includes the coloring agent in an amount of 1.5 wt % or greater with respect to an entire solid content of the second polyamide layer.

4. The catheter according to claim 1, wherein a layer thickness of the first polyamide layer is thicker than that of the second polyamide layer.

5. The catheter according to claim 1, wherein a resin forming the modified polyolefin layer is a maleated polyethylene.

6. The catheter according to claim 1, wherein the modified polyolefin layer is in direct contact with the inner surface of the first polyamide layer, and wherein the second polyamide layer is in direct contact with the outer surface of the first polyamide layer.

7. The catheter according to claim 1, wherein the modified polyolefin layer constitutes the innermost surface of the catheter tube.

8. The catheter according to claim 1, wherein the first polyamide layer and the second polyamide layer comprise the same polyamide-based resin.

9. The catheter according to claim 1, wherein the coloring agent comprises an inorganic pigment.

10. A balloon catheter, comprising:
an outer tube including a lumen;
an inner tube that is arranged in the lumen of the outer tube; and
a balloon that is fixed to a distal side of the inner tube and a distal side of the outer tube,
wherein the balloon includes a polyamide-based resin,
wherein the inner tube includes a first polyamide layer, a modified polyolefin layer arranged on an inner surface of the first polyamide layer, and a second polyamide layer arranged on an outer surface of the first polyamide layer, and
wherein among the first polyamide layer, the second polyamide layer, and the modified polyolefin layer, only the second polyamide layer includes a coloring agent.

11. The balloon catheter according to claim 10, wherein the coloring agent includes a pigment, and
wherein the second polyamide layer includes the pigment of 0.6 wt % or greater with respect to an entire solid content of the second polyamide layer.

12. The balloon catheter according to claim 10, wherein the coloring agent includes a pigment in an amount of 40 wt % or greater with respect to an entire solid content of the coloring agent, and
wherein the second polyamide layer includes the coloring agent in an amount of 1.5 wt % or greater with respect to an entire solid content of the second polyamide layer.

13. The balloon catheter according to claim 10, wherein a layer thickness of the first polyamide layer is thicker than that of the second polyamide layer.

14. The balloon catheter according to claim 10, wherein a resin forming the modified polyolefin layer is a maleated polyethylene.

15. The balloon catheter according to claim 10, wherein the modified polyolefin layer is in direct contact with the inner surface of the first polyamide layer, and wherein the second polyamide layer is in direct contact with the outer surface of the first polyamide layer.

16. The balloon catheter according to claim 10, wherein the modified polyolefin layer constitutes the innermost surface of the catheter tube.

17. The balloon catheter according to claim 10, wherein the first polyamide layer and the second polyamide layer comprise the same polyamide-based resin.

18. The balloon catheter according to claim 10, wherein the coloring agent comprises an inorganic pigment.

19. A balloon catheter, comprising:
an outer tube including a lumen;
an inner tube that is arranged in the lumen of the outer tube; and
a balloon that is fixed to a distal side of the inner tube and a distal side of the outer tube,
wherein the balloon includes a polyamide-based resin,
wherein the inner tube includes a first polyamide layer, a modified polyolefin layer arranged on an inner surface of the first polyamide layer, and a second polyamide layer arranged on an outer surface of the first polyamide layer, and
wherein an amount of a coloring agent present in the second polyamide layer is greater than an amount of the coloring agent present in the first polyamide layer, wherein an amount of the coloring agent present in the second polyamide layer is greater than an amount of the coloring agent present in the modified polyolefin layer.

20. The balloon catheter according to claim 19, wherein the first polyamide layer and the modified polyolefin layer do not include the coloring agent.

21. The balloon catheter according to claim 19, wherein a layer thickness of the first polyamide layer is thicker than that of the second polyamide layer.

* * * * *